(12) United States Patent
Kim

(10) Patent No.: US 10,589,109 B2
(45) Date of Patent: Mar. 17, 2020

(54) WEARABLE CARDIOVERTER DEFIBRILLATOR (WCD) SYSTEM COMPUTING PATIENT HEART RATE BY MULTIPLYING ECG SIGNALS FROM DIFFERENT CHANNELS

(71) Applicant: West Affum Holdings Corp., Grand Cayman (KY)

(72) Inventor: Jaeho Kim, Redmond, WA (US)

(73) Assignee: West Affum Holdings Corp., Grand Cayman (KY)

(*) Notice: Subject to any disclaimer, the term of this patent is extended or adjusted under 35 U.S.C. 154(b) by 172 days.

(21) Appl. No.: 15/927,017

(22) Filed: Mar. 20, 2018

(65) Prior Publication Data
US 2018/0289974 A1 Oct. 11, 2018

Related U.S. Application Data

(63) Continuation-in-part of application No. 15/920,505, filed on Mar. 14, 2018, now abandoned.
(Continued)

(51) Int. Cl.
*A61N 1/00* (2006.01)
*A61N 1/39* (2006.01)
(Continued)

(52) U.S. Cl.
CPC ........ *A61N 1/3904* (2017.08); *A61B 5/04011* (2013.01); *A61B 5/7217* (2013.01);
(Continued)

(58) Field of Classification Search
CPC .. A61N 1/3904; A61N 1/3987; A61N 1/3968; A61N 1/3925; A61N 1/0484;
(Continued)

(56) References Cited

U.S. PATENT DOCUMENTS

| 3,724,355 A | 4/1973 | Unger |
| 4,583,524 A | 4/1986 | Hutchins |

(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Scott M. Getzow
(74) *Attorney, Agent, or Firm* — Spectrum IP Law Group LLC

(57) ABSTRACT

A wearable cardioverter defibrillator system includes a support structure that is configured to be worn by a patient. When thus worn, the support structure may attach electrodes at different locations of the patient's body, so as to define different vectors. A measurement circuit may sense ECG signals from the different vectors substantially concurrently. A processor may multiply together these substantially concurrent ECG signals to derive a product waveform. The processor may then detect peaks in the product waveform, measure durations of time intervals between successive peaks, and determine the patient's heart rate from these durations. An advantage can be that the heart rate may be computed notwithstanding noise in the individual ECG signals.

21 Claims, 11 Drawing Sheets

SAMPLE COMPONENTS OF WEARABLE CARDIOVERTER DEFIBRILLATOR (WCD) SYSTEM

Related U.S. Application Data

(60) Provisional application No. 62/483,761, filed on Apr. 10, 2017.

(51) Int. Cl.
| | |
|---|---|
| *A61B 5/00* | (2006.01) |
| *A61B 5/04* | (2006.01) |
| *A61N 1/04* | (2006.01) |
| *A61B 5/0456* | (2006.01) |
| *A61B 5/0464* | (2006.01) |

(52) U.S. Cl.
CPC .......... *A61N 1/3987* (2013.01); *A61B 5/0456* (2013.01); *A61B 5/0464* (2013.01); *A61B 5/7235* (2013.01); *A61N 1/046* (2013.01); *A61N 1/0484* (2013.01); *A61N 1/3925* (2013.01); *A61N 1/3968* (2013.01)

(58) Field of Classification Search
CPC ..... A61N 1/046; A61B 5/04011; A61B 5/024; A61B 5/0452; A61B 5/72; A61B 5/7203–7217; A61B 5/7217; A61B 5/7235; A61B 5/0464; A61B 5/0456
See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Nay et al. | |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,437,083 B1 | 8/2002 | Brack et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,644,925 B2 | 2/2014 | Volpe et al. | |
| 8,738,130 B2 | 5/2014 | Freeman et al. | |
| 8,897,860 B2 | 11/2014 | Volpe et al. | |
| 8,949,077 B2 | 2/2015 | Fu et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0302860 A1 | 11/2012 | Volpe et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2016/0004831 A1 | 1/2016 | Carlson et al. | |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

SAMPLE COMPONENTS OF WEARABLE CARDIOVERTER DEFIBRILLATOR (WCD) SYSTEM

SAMPLE COMPONENTS OF EXTERNAL DEFIBRILLATOR

*ELECTRODES & ECG SIGNALS ALONG MULTIPLE VECTORS*

WEARABLE CARDIOVERTER DEFIBRILLATOR (WCD) SYSTEM COMPUTING PATIENT HEART RATE BY MULTIPLYING ECG SIGNALS FROM DIFFERENT CHANNELS

CROSS REFERENCE TO RELATED PATENT APPLICATIONS

This patent application is a Continuation In Part of copending U.S. patent application Ser. No. 15/920,505, filed on Mar. 14, 2018, and further claims priority from U.S. Provisional Patent Application Ser. No. 62/483,761, filed on Apr. 10, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

A challenge in the prior art is that the patient's ECG signal may be corrupted by electrical noise. As such, it can be hard to interpret the ECG signal.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor. This approach in and of itself may also be inventive.

BRIEF SUMMARY

The present description gives instances of wearable cardioverter defibrillator (WCD) systems, storage media that store programs, and methods, the use of which may help overcome problems and limitations of the prior art.

In embodiments, a wearable cardioverter defibrillator system includes a support structure that is configured to be worn by a patient. When thus worn, the support structure may attach electrodes at different locations of the patient's body, so as to define different vectors. A measurement circuit may sense ECG signals from the different vectors substantially concurrently. A processor may multiply together these substantially concurrent ECG signals to derive a product waveform. The processor may then detect peaks in the product waveform, measure durations of time intervals between successive peaks, and determine the patient's heart rate from these durations. An advantage can be that the heart rate may be computed notwithstanding noise in the individual ECG signals.

These and other features and advantages of the claimed invention will become more readily apparent in view of the embodiments described and illustrated in this specification, namely in this written specification and the associated drawings.

DETAILED DESCRIPTION

As has been mentioned, the present description is about wearable cardioverter defibrillator (WCD) systems, and related storage media, programs and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
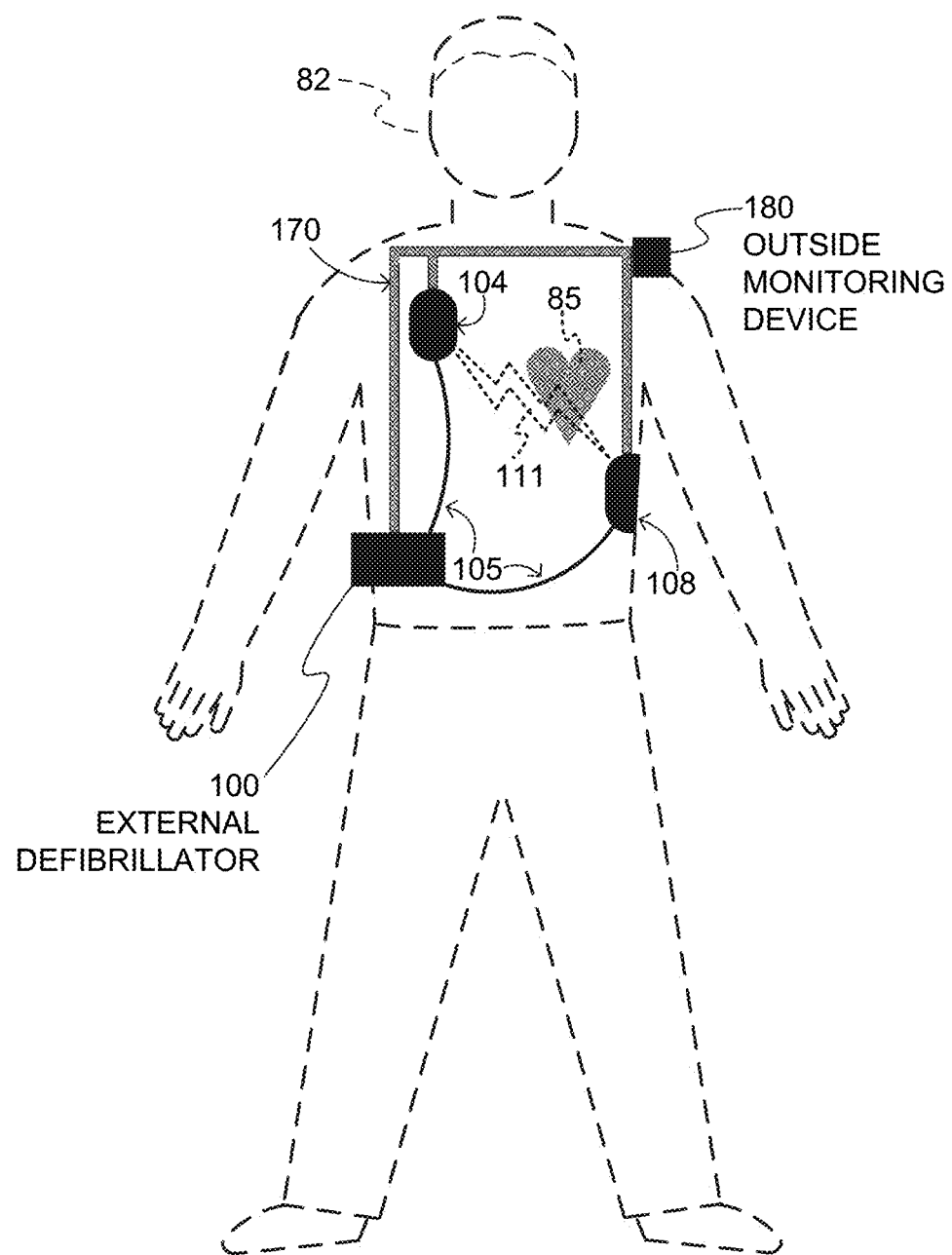
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
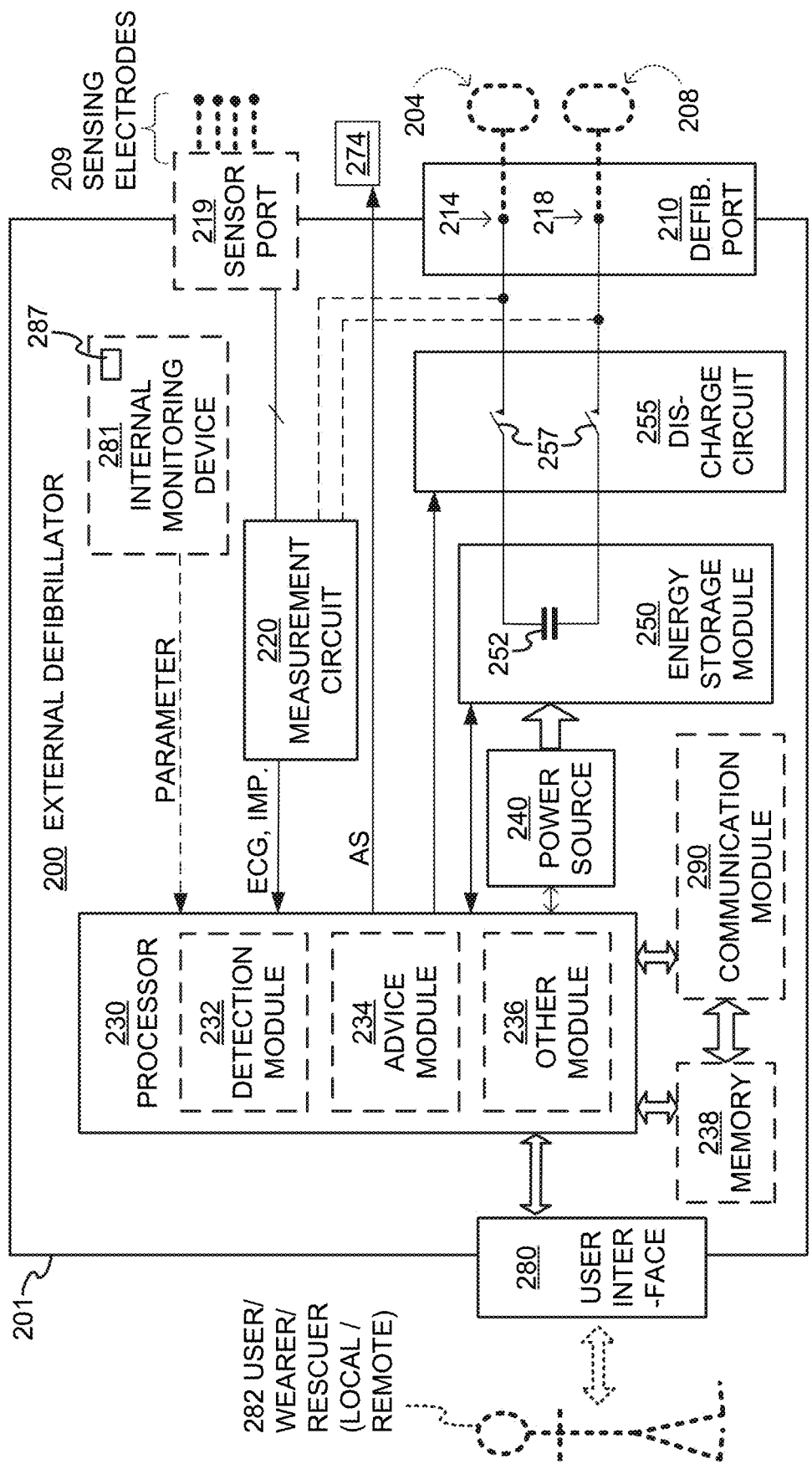
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

Figure 3:
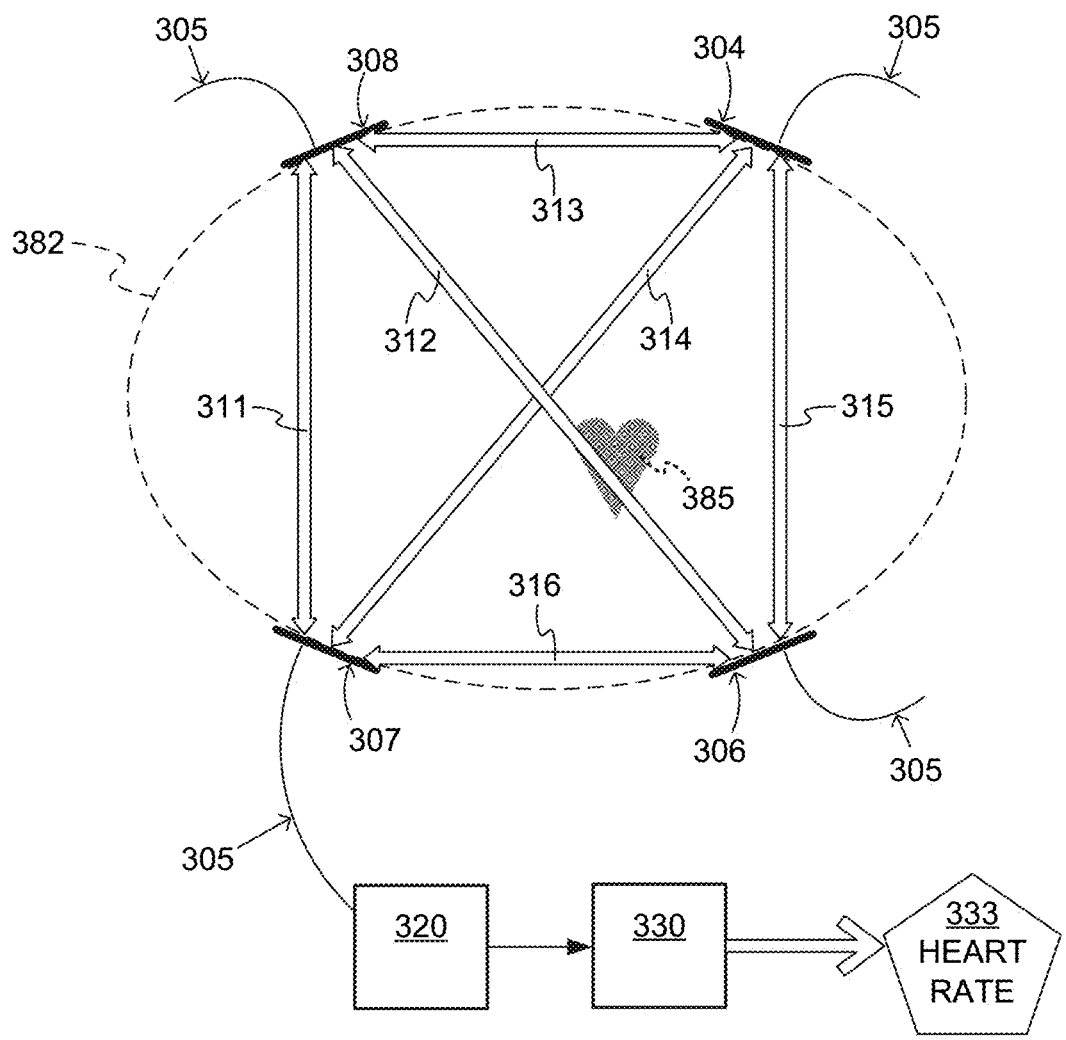
FIG. 3 is a conceptual diagram for illustrating how different electrodes may sense ECG signals of the patient along different vectors according to embodiments.

FIG. 3 is a conceptual diagram for illustrating how electrodes of a WCD system may sense or capture ECG signals along different vectors according to embodiments. A section of a patient 382 having a heart 385 is shown. There are four electrodes 304, 306, 307, 308, attached to different locations of the torso of patient 382, each with a wire lead 305. Any pair of these electrodes defines a vector, across which an ECG signal may be measured. These vectors are also known as channels and ECG channels. The four electrodes 304, 306, 307, 308 therefore can define six vectors, across which six respective ECG signals 311, 312, 313, 314, 315, 316 can be sensed. FIG. 3 thus illustrates a multi-vector situation. In FIG. 3 it will be understood that electrodes 304, 306, 307, 308 are drawn on the same plane for simplicity, while that is not necessarily the case. Accordingly, the vectors of ECG signals 311-316 are not necessarily on the same plane, either.

Any one of ECG signals 311-316 might provide sufficient data for making a shock/no shock determination. The effort is to shock when needed, and not shock when not needed. The problem is that, at any given point in time, some of these ECG signals may include noise, while others not. The noise may be due to patient movement or how well the electrodes contact the skin. The noise problem for a WCD may be further exacerbated by the desire to use dry, non-adhesive monitoring electrodes. Dry, non-adhesive electrodes are thought to be more comfortable for the patient to wear in the long term, but may produce more noise than a conventional ECG monitoring electrode that includes adhesive to hold the electrode in place and an electrolyte gel to reduce the impedance of the electrode-skin interface.

FIG. 3 also shows a measurement circuit 320 and a processor 330, which can be made as described for measurement circuit 220 and processor 230 later in this document. Processor 330 may further compute a heart rate 333 according to embodiments, as described in more detail further in this document.

Returning to FIG. 2, defibrillator 200 also includes a measurement circuit 220, as one or more of its sensors or transducers. Measurement circuit 220 can be configured to sense one or more electrical physiological signals of the patient from sensor port 219, if provided. For instance, measurement circuit 220 can be configured to sense Electrocardiogram (ECG) signals, as measurement circuit 320 can be configured to sense ECG signals from different vectors. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input reflects an ECG measurement. The patient parameter can be an ECG, which can be sensed as a voltage difference between electrodes 204, 208. In addition the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. For instance, signals sensed as voltages can be digitized to become numbers by an Analog to Digital Converter (ADC). In embodiments, the signals are sampled at a high frequency, and the result is simply a group of values—voltage or impedance—as a function of time passing.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are sensed or captured according to embodiments, and determining whether a shock criterion is met. The determination can be made from a rhythm analysis of the sensed or captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

In embodiments, values of a first ECG signal are multiplied with values of a second ECG signal, in order to derive a product waveform. The processing of such multiplying and other operations may be done by processor 230 or processor 330. Examples are now described.

Figure 4:
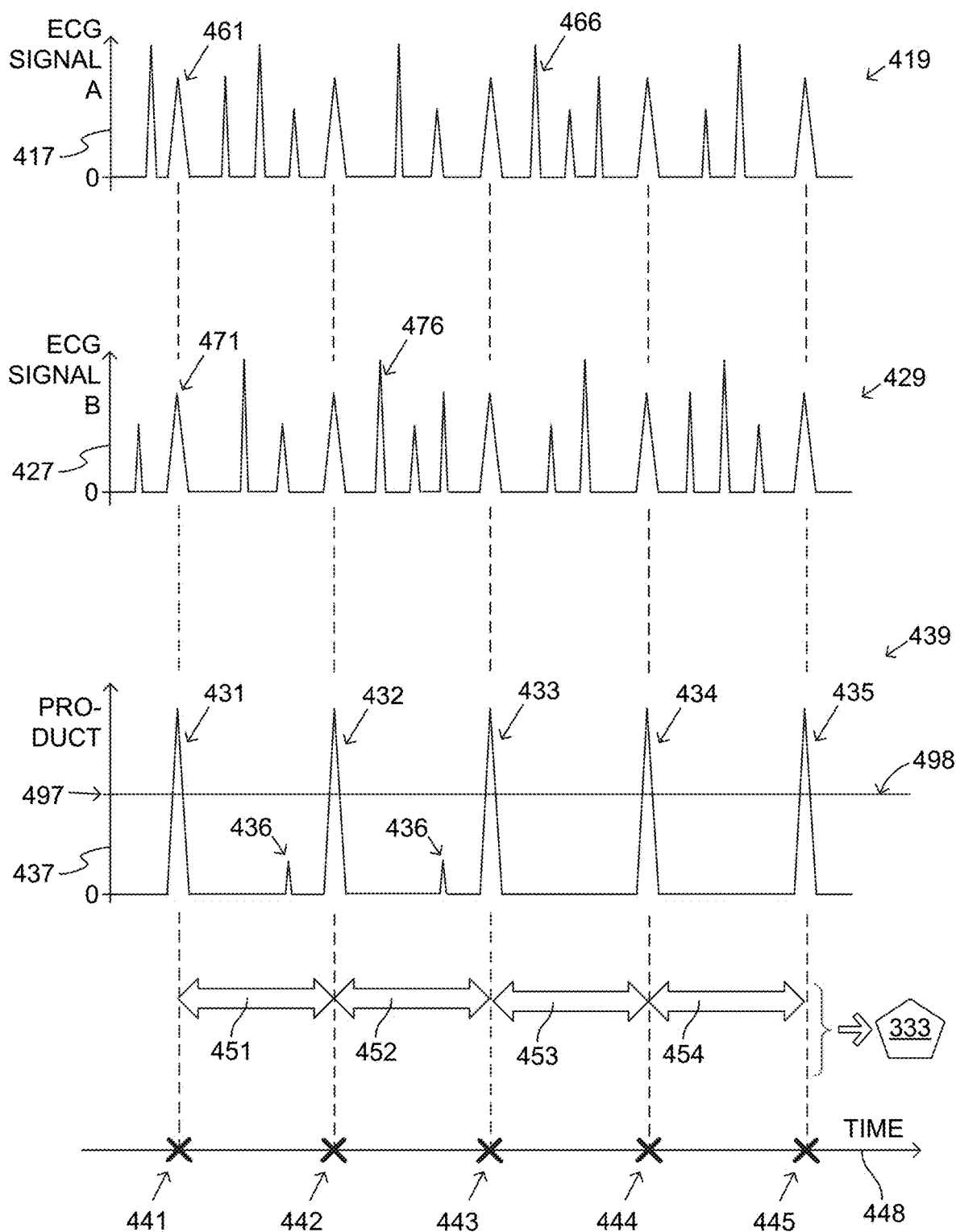
FIG. 4 shows time diagrams that illustrate sample generalized noisy ECG signals, their product waveform, and how that product waveform may be used to determine the patient's heart rate according to embodiments.

FIG. 4 shows time diagrams using a single time axis 448. A diagram 419 shows the amplitude of a first ECG signal A from a first vector on a vertical semi-axis 417. The signal could be digitized, and its values sampled quickly enough to where the depicted signal waveform appears as a continuous line in FIG. 4, which is good enough for purposes of the description of FIG. 4. First ECG signal A is shown as generalized—in this instance as having upward-going peaks from a baseline value of zero. Again, this generalization is good enough for purposes of the description of FIG. 4. The reason is that these peaks could be from true ECG features such as QRS complexes, or from noise.

FIG. 4 also shows a diagram 429 of a second ECG signal B from a second vector, whose amplitude is shown against a vertical semi-axis 417. The same considerations apply as in diagram 419. From shared time axis 448, it will be appreciated that second ECG signal B is sensed substantially contemporaneously with when the first ECG signal was sensed.

In each of diagrams 419 & 429 taken by itself, processor 330 may not be able to discern whether an individual peak is generated from a true ECG feature or from noise. For example, in diagram 419, each of peaks 461 and 466 could be either from a true ECG feature of first ECG signal A, or from noise in the first channel that delivered first ECG signal A. The same applies also for peaks 471 & 476 in diagram 429, about second ECG signal B and the second channel that delivered second ECG signal B.

In embodiments, processors 230 and 330 discern the difference in what generated the individual peaks of diagrams 419 and 429. And, disregarding peaks generated from noise, processors 230 and 330 may use peaks generated by true ECG features to determine the value heart rate 333. And that value alone may determine whether a rhythm is shockable or not, regardless of whether the ECG features that generated these peaks are QRS complexes, which would be slower and at a lesser heart rate, or portions of the zig-zag of a VT or a VF waveform, which would be faster and at a faster heart rate. Examples are now described.

FIG. 4 further shows a diagram 439, with a vertical semi-axis 437 against time axis 448. Diagram 439 shows a product waveform that has been generated according to embodiments by multiplying values of first ECG signal A with values of second ECG signal B. As such, the units of vertical semi-axis 437 are voltage times voltage, or (Volts)$^2$. In other words, the product waveform of diagram 439 is not a depiction of an ECG signal, or even of a voltage signal; rather, the product waveform of diagram 439 is a depiction of a useful construct according to embodiments.

The product waveform of diagram 439 has zero values where either first ECG signal A or second ECG signal B has a zero value. And, the product waveform has non-zero values everywhere else. In addition, the product waveform has tall peaks 431, 432, 433, 434, 435, which is where tall peaks of first ECG signal A coincide substantially with tall peaks of second ECG signal B. Moreover, the product waveform has short peaks 436 where the peaks of first ECG signal A coincide only a little with the peaks of second ECG signal B, or where one of these coincident peaks is not tall.

In embodiments, peaks in diagram 439 that exceed a detection threshold are detected in the product waveform. Such detection may be performed by processors 230, 330. For example, in diagram 439, a detection threshold is shown by a line 498 that has a fixed value 497. Tall peaks 431, 432, 433, 434, 435 exceed detection threshold 498, and are thus detected. Short peaks 436 do not exceed detection threshold 498, and are thus not detected and disregarded. The detected tall peaks 431, 432, 433, 434, 435 may be deemed to be generated from features of the patient's true ECG signal, which were transmitted from both channels, because the ECG signal was the same in each channel. The short peaks 436 may be disregarded because they are deemed to be generated from noise in the channels, because noise may be generated independently in each channel, which means at different moments for each channel and with different amplitudes for each channel. To the extent it is of interest to look back at diagrams 419, 429, now it is known that peaks 461, 471 were from a true ECG feature, while peaks 466, 476 were from noise.

As seen on time axis 448, detected peaks 431, 432, 433, 434, 435 occur at times 441, 442, 443, 444, 445. In embodiments, time intervals are defined between pairs of successive ones of the detected peaks. As such, time interval 451 is defined between peaks 431 & 432; time interval 452 is defined between peaks 432 & 433; time interval 453 is defined between peaks 433 & 434; and time interval 454 is defined between peaks 434 & 435.

In embodiments, durations of these time intervals 451, 452, 453, 454 are measured, and a heart rate 333 of the patient is computed from these measured durations. Such computing may be done by processor 230 or processor 330. Since detected peaks 431, 432, 433, 434, 435 are substantially evenly spaced in time, the computation of heart rate 333 will be rather reliable.

In embodiments, it can be determined from the computed heart rate, or from a subsequent ECG signal, whether or not a shock criterion is met. For example, a fast heart rate may indicate VF or VT, and so on. If so, responsive to the shock criterion being met, discharge circuit 255 can be controlled by processor 230 or 330 to discharge the stored electrical charge through patient 82, while support structure 170 is worn by patient 82 so as to deliver shock 111 to patient 82.

It may be observed that, determining heart rate 333 from tall peaks 431, 432, 433, 434, 435 is similar to determining a heart rate from a series of QRS peaks. It should be remembered, however, that the product waveform of time diagram is not an ECG signal—even the units of the amplitude are different.

It will be appreciated that the operations of FIG. 4 may happen in real time. For example, the ECG signals of diagrams 419 and 429 may be acquired, optionally processed such as with high-pass-filtering and perhaps additional operations, and the product waveform may be computed again in real time. Or, the signals may be stored, and then processed.

In the example of FIG. 4, the baseline value of diagrams 419 & 429 is zero. That is not, however, necessary for implementing the invention. Indeed, even if the baseline value were not zero, a similar phenomenon may result. In particular, in the product waveform, the patient's ECG signal being sensed concurrently in all the channels may generate taller peaks that can be useful for determining the heart rate, while noise generated independently in each channel may generate relatively shorter peaks that can be disregarded.

While not necessary, it is preferred that the baseline value of diagrams 419 & 429 be zero, since this may shorten the computations. Indeed, multiplying by zero results in zero, which requires lesser processing. As such, in some embodiments, processor 230, 330 is further configured to high-pass filter at least one or both of first ECG signal A and second ECG signal B, so as to derive a high-pass filtered first ECG signal, and a high-pass filtered second ECG signal. In such embodiments, the product waveform may be derived by multiplying values of the high-pass filtered first ECG signal instead of multiplying values of the first ECG signal, and so on with the second signal. A good value for the high-pass filtering is 8 Hz. In those instances, what is shown in diagrams 419, 429 would be high-pass filtered versions of the ECG signals, instead of the ECG signals themselves.

The examples of FIG. 4 were shown with generalized ECG signals. Examples are now given with non-generalized ECG signals.

Figure 5A:
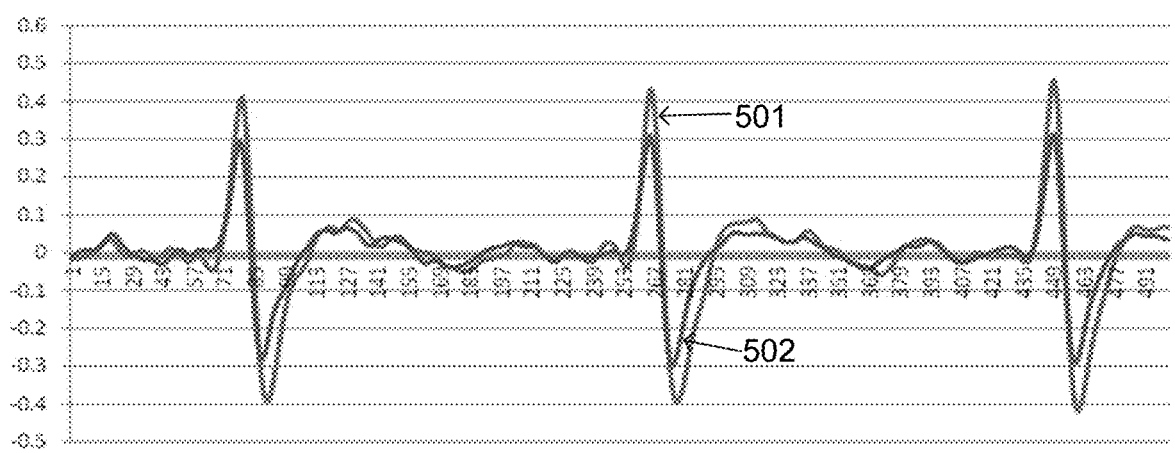
FIG. 5A is a time diagram of two sample noise-free ECG signals from different vectors, superimposed according to embodiments.
Figure 5B:
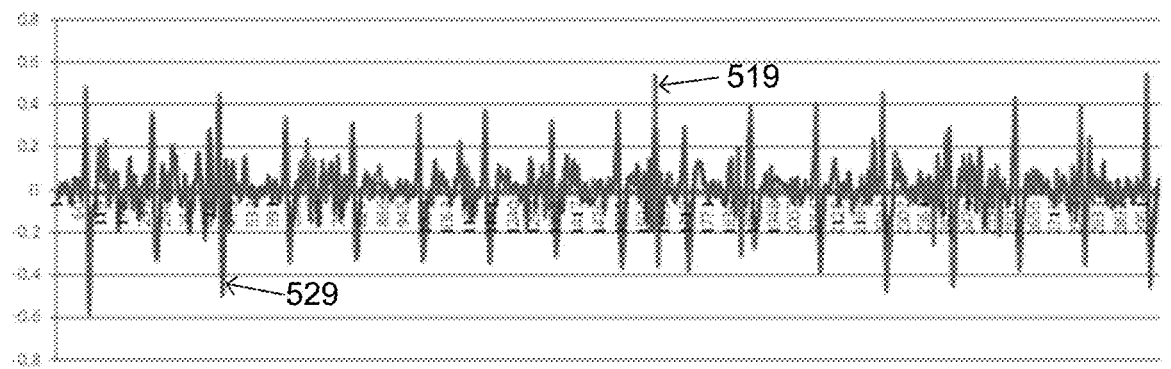
FIG. 5B is a time diagram of noisy versions of the ECG signals of FIG. 5A.

FIG. 5A is a time diagram of two sample noise-free ECG signals 501, 502 from two different vectors, superimposed according to embodiments. FIG. 5B is a time diagram of noisy versions 519, 529 of ECG signals 501, 502. Noisy ECG signals 519, 529 are shown on the same axis, which is different from FIG. 4 that shows these signals in separate diagrams 419, 429.

Figure 5C:
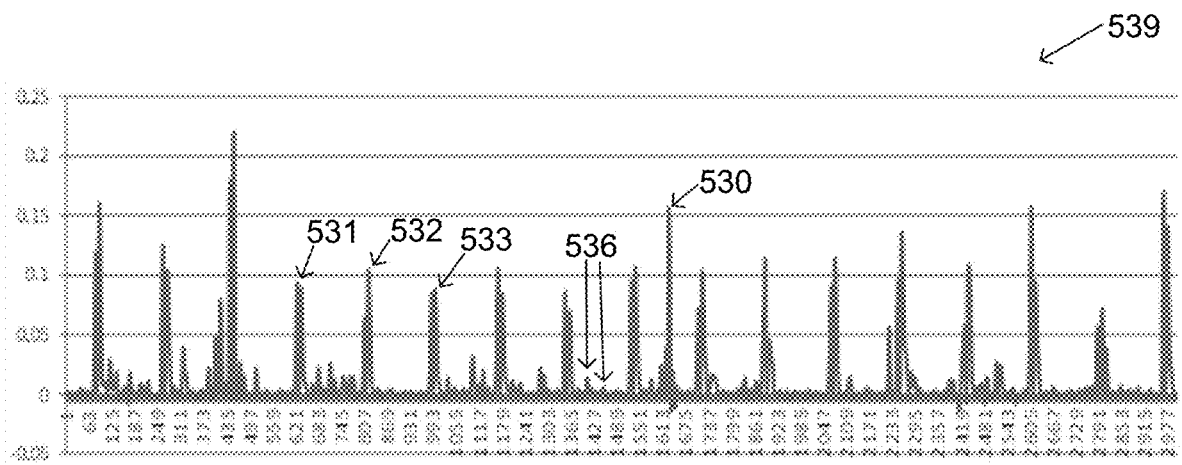
FIG. 5C is a time diagram of a product waveform of the ECG signals of FIG. 5B according to embodiments.

FIG. 5C is a time diagram 539 of a product waveform of the ECG signals of FIG. 5B according to embodiments. It will be appreciated that this product waveform has at least three tall peaks 531, 532, 533 that are substantially evenly spaced in time. Moreover, this product waveform has short peaks 536, which can be ignored. In addition, this product waveform has a spurious tall peak 530 that is not part of the evenly spaced pattern; one can tell by inspection that peak 530 is noise that may complicate the processor's computation of heart rate 333. Spurious tall peak 530 may have arisen in a number of ways. One such way is from a noise event at a single electrode that affected similarly the ECG signals in two channels, if these two ECG signals are the ones being multiplied for this product waveform.

Figure 6A:
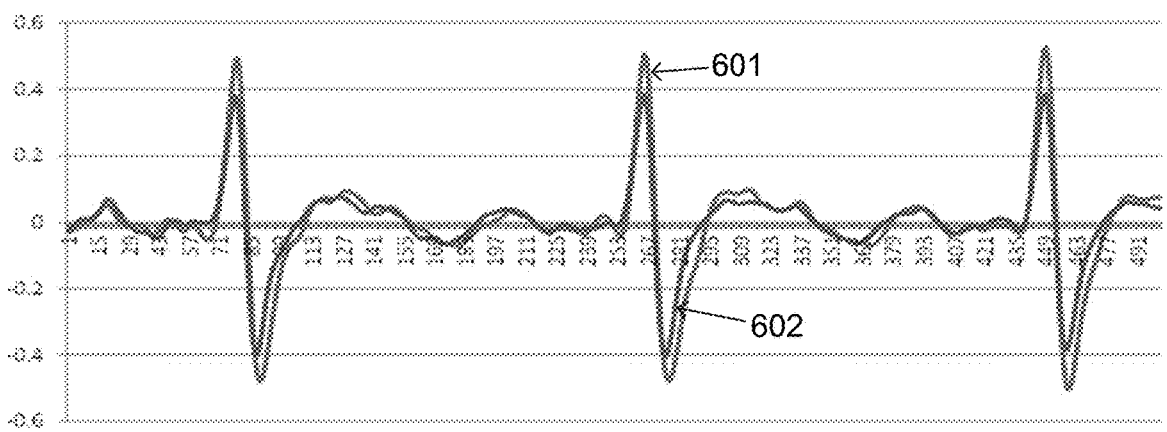
FIG. 6A is a time diagram of two sample noise-free ECG signals from different vectors, superimposed according to embodiments.
Figure 6B:
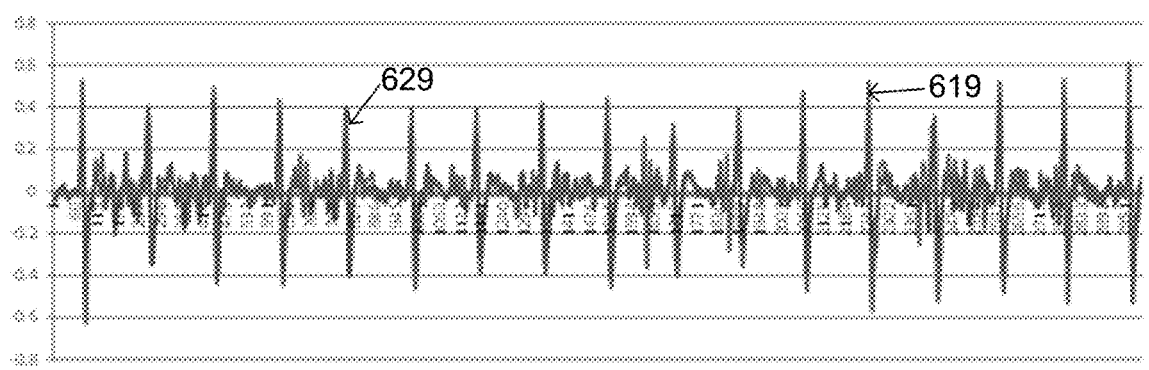
FIG. 6B is a time diagram of noisy versions of the ECG signals of FIG. 6A.
Figure 6C:
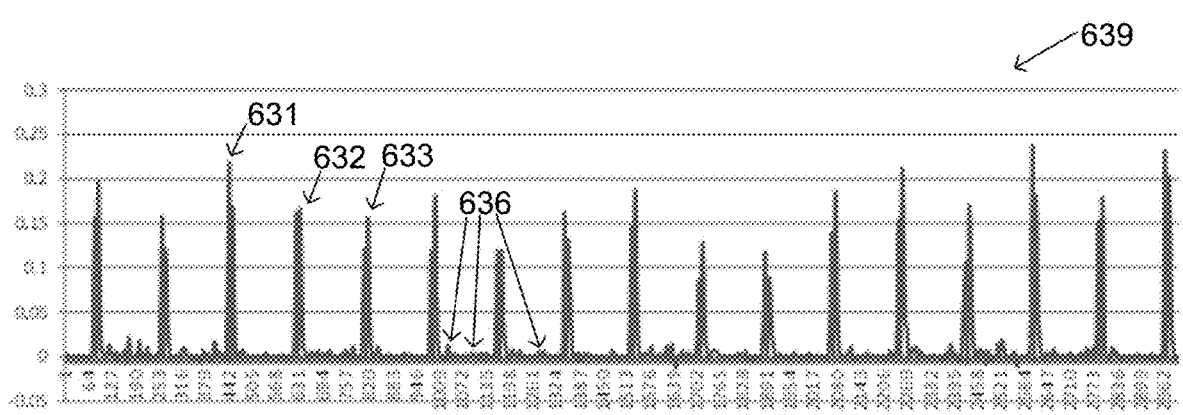
FIG. 6C is a time diagram of a product waveform of the ECG signals of FIG. 6B according to embodiments.

FIG. 6A is a time diagram of two sample noise-free ECG signals 601, 602 from another two different vectors, superimposed according to embodiments. FIG. 6B is a time diagram of noisy versions 619, 629 of ECG signals 601, 602, shown on the same axis. FIG. 6C is a time diagram 639 of a product waveform of the ECG signals of FIG. 6B according to embodiments. It will be appreciated that this product waveform has at least three tall peaks 631, 632, 633 that are substantially evenly spaced. Moreover, this product waveform has short peaks 636, which can be ignored.

In some embodiments, product waveforms can be made from ECG signals of more than two vectors or channels, for amplified effect. For example, the electrodes may further define additional vectors, such as a third vector, a fourth vector and so on. In such embodiments, measurement circuits 220, 320 can be further configured to sense a third ECG signal from the third vector, a fourth ECG signal from the fourth vector, and so on. Moreover, processors 230, 330 can be further configured to multiply values of the third ECG signal with the values of the first ECG signal and of the second ECG signal to derive the product waveform. In such a case, the product waveform may be made from three ECG signals, not just two.

Moreover, processor 230, 330 can be further configured to multiply values of the fourth ECG signal with the values of the first ECG signal, of the second ECG signal and of the third ECG signal, to derive the product waveform. In such a case, the product waveform may be made from four ECG signals, not just three.

Figure 13:
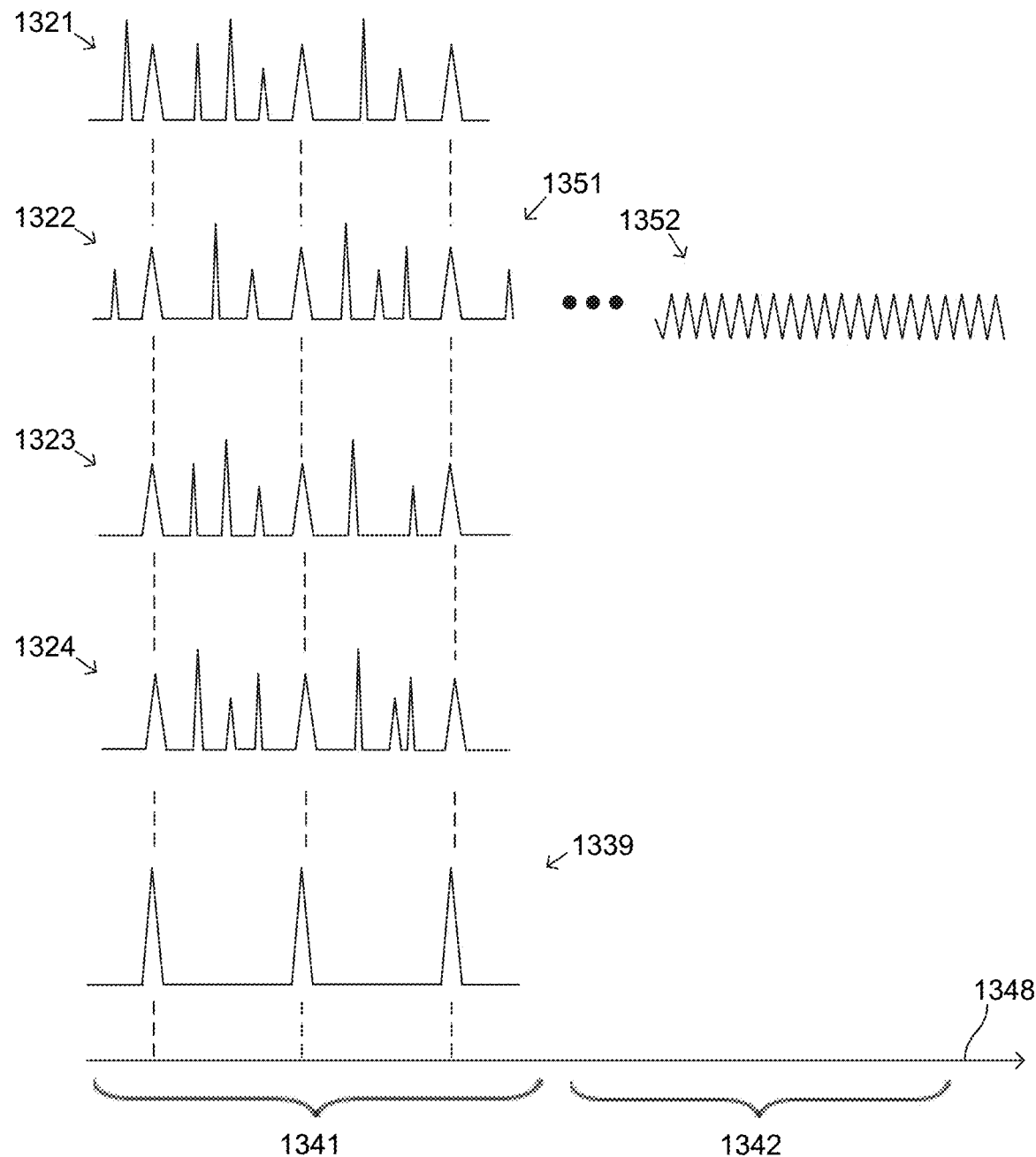
FIG. 13 is a time diagram for illustrating time relationships among various ECG signals from various channels in a sample contingency according to embodiments.

An example of using more than two ECG signals to derive a product waveform is now described. FIG. 13 is a diagram of the amplitudes of various ECG signals against a time axis 1348, which has events in two time domains 1341, 1342. ECG signals 1321, 1322, 1323, 1324 from four channels are shown, which could be taken from signals 419, 429, 519, 529, 619, 629. In the first time domain 1341, these ECG signals 1321, 1322, 1323, 1324 are substantially concurrent, and are multiplied together to generate a product waveform 1339.

In FIG. 13, the contingency is that the patient suffers SCA during the second time domain 1342. At that time, a subsequent ECG signal 1352 is sensed, and a diagnosis is made. A person skilled in the art will recognize that ECG signal 1352 likely denotes VF or VT, which calls for defibrillation. ECG signal 1352 could be sensed from any of the channels that generated these ECG signals 1321, 1322, 1323, 1324, or another ECG signal; here ECG signal 1352 is shown as being from the same channel as ECG signal 1322, but that is only by way of example. And, artificially, FIG. 13 does not show the ECG signals sensed by the other channels during subsequent time domain 1342; if these had been also shown, they would show a pattern similar to that of ECG signal 1352. Plus, the VT or VF of second time domain 1342 can also be sensed by the product waveform of the ECG signals from two or more of the channels. During time domain 1342, however, sensing ECG signal 1352 from a single ECG channel may be enough, because the patient may be motionless, and much source of ECG noise may no longer be present.

Figure 7:
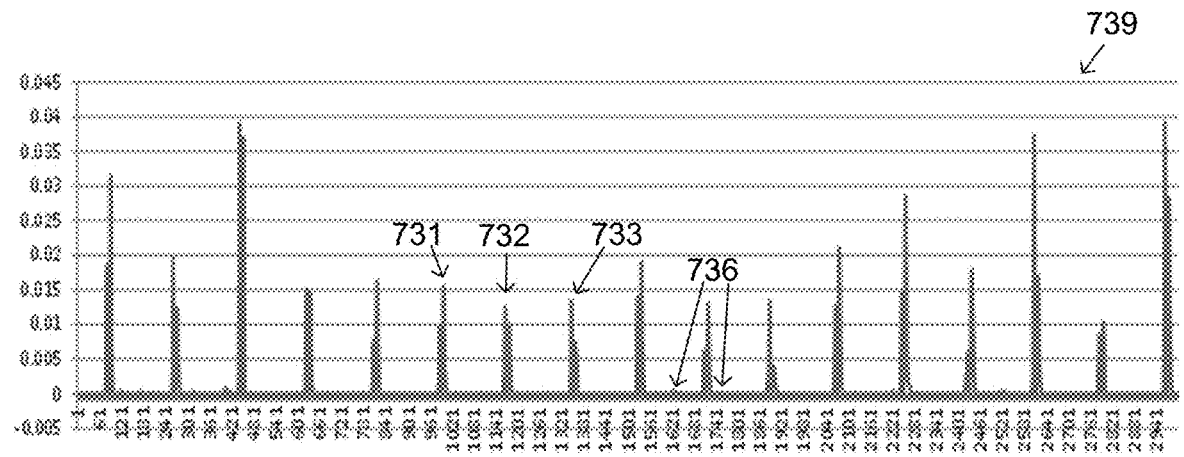
FIG. 7 is a time diagram of a product waveform that can be derived by multiplying the product waveform of FIG. 5C with the product waveform of FIG. 6C according to embodiments.

An example of the amplified effect of using more than two ECG signals to derive the product waveform is now described. FIG. 7 is a time diagram 739 of the product waveform that can be derived by multiplying the product waveform of FIG. 5C with the product waveform of FIG. 6C. As such, the product waveform of time diagram 739 is from four distinct channels.

It will be observed that time diagram 739 has at least three tall peaks 731, 732, 733 that are substantially evenly spaced in time, and short peaks 736 that can be disregarded in the computation of heart rate 333. This aspect is similar with the product waveforms of FIGS. 5C and 6C, each of which was made from only two ECG signals.

It will be appreciated that the product waveform of FIG. 7 is improved over those of FIG. 5C and FIG. 6C. These improvements make it easier to distinguish the valid peaks from the peaks to disregard, for computing heart rate 333.

One improvement is that the product waveform of diagram 739 has no spurious tall peaks, of the type of peak 530 in FIG. 5C.

Another improvement is in the ratio of the amplitude of tall peaks 731, 732, 733 over short peaks 736. This ratio is larger in FIG. 7 than in FIGS. 5C and 6C. In other words, in FIG. 7 the usable tall peaks became taller while the short peaks became shorter, which is a phenomenon that makes them even easier to differentiate from each other and ultimately discard the short peaks.

One more improvement is that tall peaks 731, 732, 733 are narrower. There are fewer peaks of medium height immediately before and immediately after the very tall peaks. Such medium-height peaks might introduce ambiguity in the detection of when the tall peak occurred. The fewer the medium-height peaks, the less ambiguity will there be in such detection, because it will be easier to set the detection threshold.

Detection is now described in more detail. In some embodiments, when a peak is detected at a certain moment, no other peaks are detected for an inactive time period after the certain moment. An example is now described.

Figure 8:
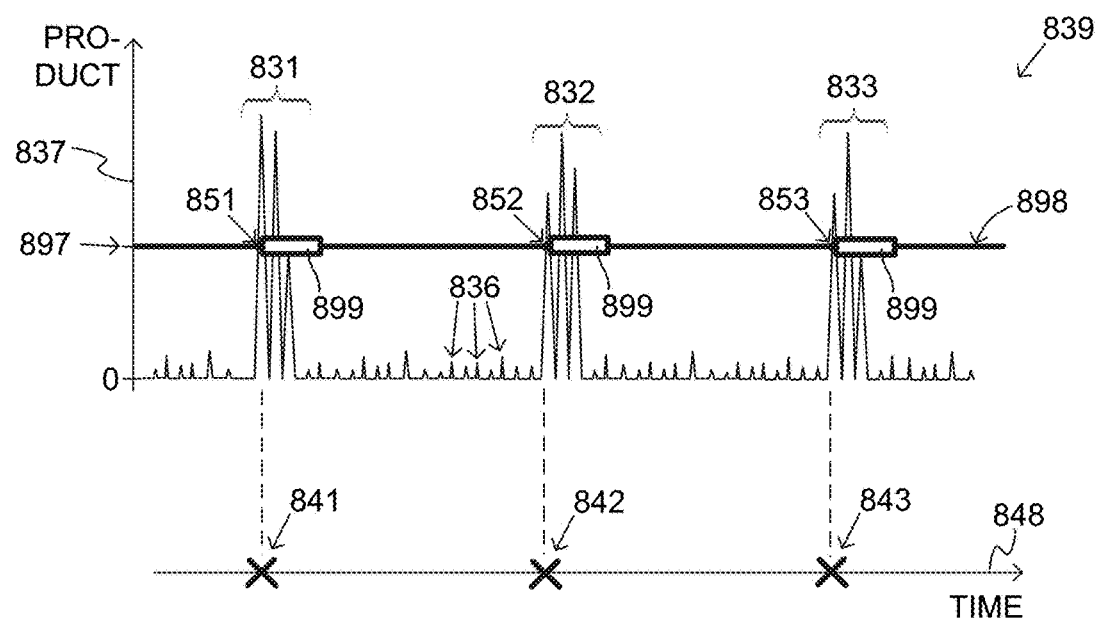
FIG. 8 is a time diagram for illustrating how peaks may be detected in a sample product waveform according to embodiments with a fixed detection threshold.

FIG. 8 is a time diagram 839, which uses a time axis 848 and a vertical semi-axis 837. Time diagram 839 depicts another product waveform. While, however, it was mentioned with reference to FIG. 4 that a signal waveform appears as a continuous line and that was good enough for FIG. 4, for the detection of FIG. 8 granularity may start to appear due to fine sampling. Even when it does, this recognition is not a problem. So, the product waveform in time diagram 839 has three tall peak groups 831, 832, 833, and multiple small peaks 836. The granularity is that each of peak groups 831, 832, 833 actually has multiple tall peaks due to the fine sampling.

In diagram 839, a detection threshold is shown by a line 898 that has a fixed value 897. Short peaks 836 do not exceed detection threshold 898, and are thus not detected and disregarded. For the taller peaks, a detection event happens at detection point 851, when the first tall peak of peak group 831 exceeds value 897. After detection point 851, detection is disabled for an inactive time period 899, during which no other peak is detected. As such, none of the other peaks of peak group 831 are detected, and the whole peak group 831 is detected only once. Similarly, another detection event happens at detection point 852, when the first tall peak of peak group 832 exceeds value 897. Detection point 852 is followed by another inactive time period 899. And one more detection event happens at detection point 853, when the first tall peak of peak group 833 exceeds value 897. Detection point 853 is followed by another inactive time period 899.

In FIG. 8, detection points 851, 852, 853 happen at respective time moments 841, 842, 843. Heart rate 333 can then be computed from durations between time moments 841, 842, 843. It is preferred to set the duration of inactive time period 899 to be short enough so as to not interfere with expected values of the heart rate.

In FIG. 8, detection threshold 898 was constant. In fact, it was at a good value 897, given what needs to be detected and what needs to be discarded. Good such values may be learned with time. In some embodiments, however, the detection threshold may change with time, dynamically, in anticipation of the amplitude and timing of the next peak that should be detected. In some embodiments, responsive to a certain one of the peaks being thus detected, a certain amplitude of the certain detected peak is input in the processor, for example in a memory register and so on. In such embodiments, the detection threshold can be then established for later use responsive to the input certain amplitude. Examples of such embodiments are now described.

Figure 9:
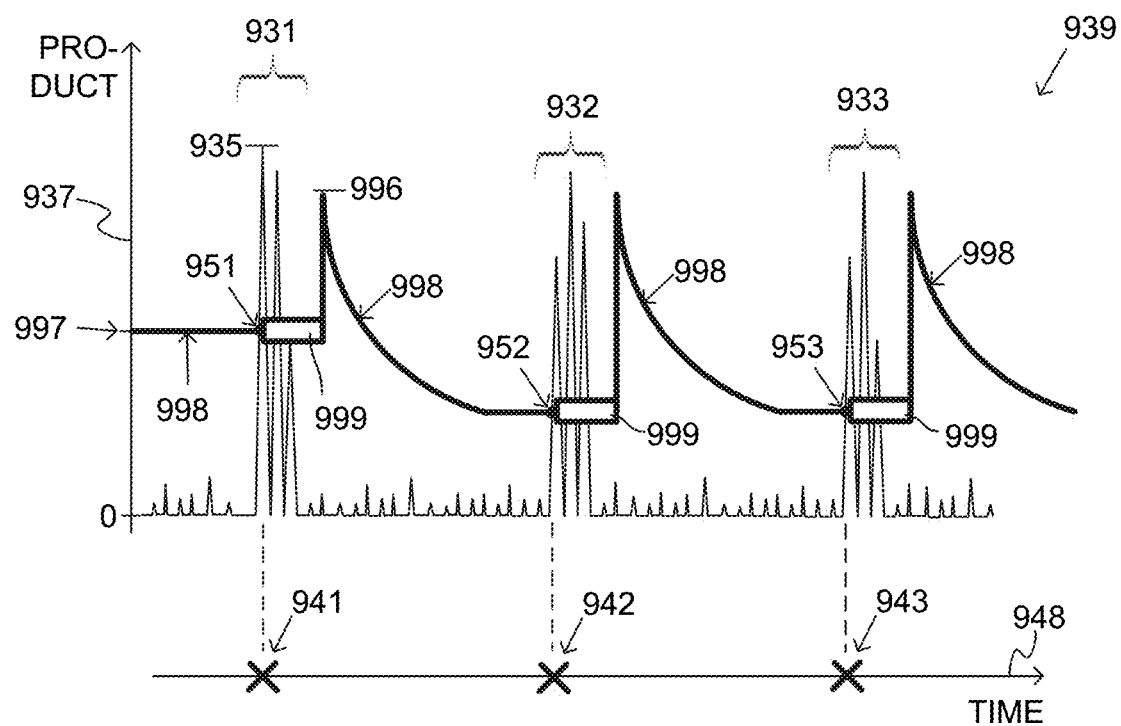
FIG. 9 is a time diagram for illustrating how peaks may be detected in a sample product waveform according to embodiments with a variable detection threshold.

FIG. 9 is a time diagram 939, which uses a time axis 948 and a vertical semi-axis 937. Time diagram 939 depicts one more product waveform, which has three tall peak groups 931, 932, 933, and multiple small peaks that are disregarded.

In diagram 939, a detection threshold is shown by a line 998 whose value changes with time. The value starts with a fixed value 997 until a detection event happens at detection point 951, which is from the first tall peak of peak group 931. At that time, a certain amplitude of the certain detected peak is input. That certain amplitude is shown as a value at a height 935, with a very short horizontal line. Then an inactive time period 999 follows. At the end of this inactive time period, the detection threshold 998 is then established responsive to the input certain amplitude. As such, it becomes initially established at a value 996, which is determined from the value at height 935. Then detection threshold 998 can drop exponentially, until it reaches a lower value and stay at that lower value. The lower value can be, for example, a fraction of value 996. While at that lower value, a detection event happens at detection point 952, which may be followed by another inactive time period 999, then resetting the detection threshold 998 at a higher value, and so on. One more detection event happens at detection point 953. Detection points 951, 952, 953 happen at respective time moments 941, 942, 943. Heart rate 333 can then be computed from durations between time moments 941, 942, 943, as per the above.

Figure 10:
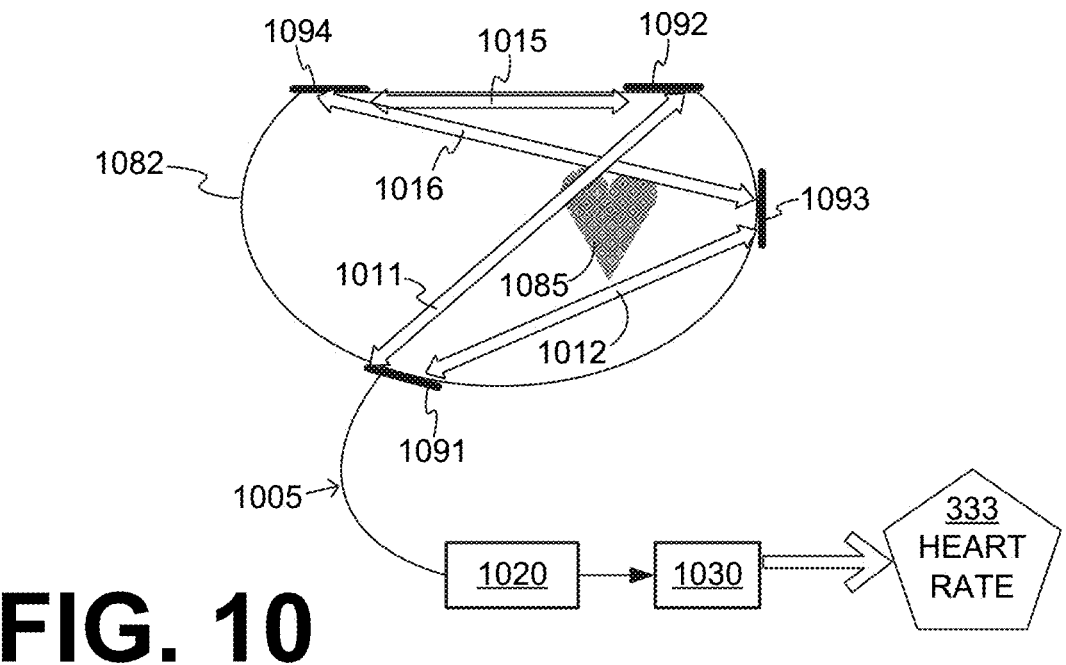
FIG. 10 is a diagram for illustrating an example of why ECG signals of the patient sensed along different vectors according to embodiments may be initially unsynchronized.

More refinements are now described. FIG. 10 shows a section of a patient 1082 having a heart 1085. In FIG. 10, patient 1082 is viewed from the top, and is facing down. Given this orientation, heart 1085 is on the right hand side within the torso. A measurement circuit 1020 and a processor 1030 can be made as described for measurement circuits 220, 320 and for processors 230, 330. Processor 1030 may further compute heart rate 333 according to embodiments.

Patient 1082 is wearing a support structure, which is not shown in FIG. 10 for simplicity. The support structure attaches or applies four electrodes 1091, 1092, 1093, 1094 to different locations of the torso of patient 1082. Each electrode may have a wire lead, which leads to measurement circuit 1020. One of these wire leads is shown as wire lead 1005. Any pair of electrodes 1091, 1092, 1093, 1094 defines a vector, across which an ECG signal may be sensed or measured. The discussion for FIG. 10 is only for vectors 1011, 1012, 1015, 1016.

Heart 1085 is the source of the ECG signal. Because electrodes 1092 & 1093 are near the source of the ECG signal, and electrodes 1091 & 1094 are away from the heart, the QRS morphologies of ECG signals sensed or measured between vectors 1011, 1012, 1015, 1016 can be both similar and also synchronized. These aspects, namely similarity in morphology and synchronization, can increase the amplitude of the tall peaks in a product waveform.

In some embodiments, the ECG signals might not start out as synchronized. In such embodiments, one of the signals is time-shifted with respect to the other to derive a time-shifted ECG signal, and the product waveform is derived by multiplying values of the time-shifted ECG signal instead of multiplying values of the ECG signal before it was time shifted. An example is now described.

Figure 11:
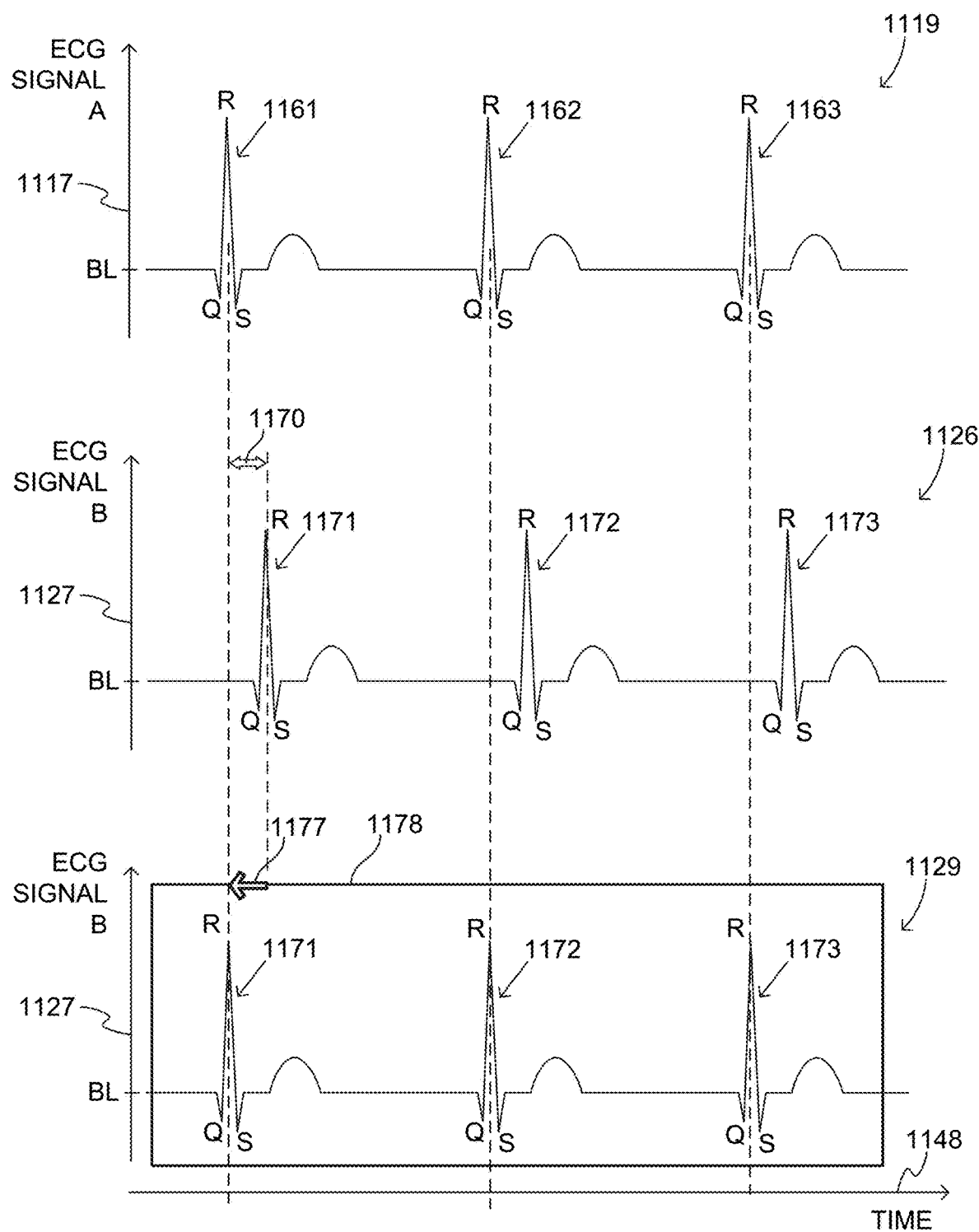
FIG. 11 shows time diagrams for illustrating how ECG signals from different channels can become synchronized according to embodiments.

FIG. 11 shows time diagrams across a time axis 1148. A diagram 1119 has a vertical amplitude semi-axis 1117, and shows the waveform of an idealized, noise-free first ECG signal A. ECG signal A is centered around a baseline BL, and has three QRS complexes 1161, 1162, 1163.

In addition, a diagram 1126 has a vertical amplitude semi-axis 1127, and shows the waveform of an idealized, noise-free second ECG signal B. ECG signal B is centered around a baseline BL, and has three QRS complexes 1171, 1172, 1173. It will be observed that second ECG signal B is delayed with respect to first ECG signal A by a time lag 1170. The time lag may arise due to the vectors having differing distances from the heart, and so on.

As mentioned above, processors 230, 330, 1030 may be configured to time-shift second ECG signal B with respect to first ECG signal A, so as to derive a time-shifted second ECG signal. For example, one more diagram 1129 in FIG. 11 repeats semi-axis 1127. In addition, it shows a box 1178 that repeats the portion of the signal of diagram 1126 that includes QRS complexes 1171, 1172, 1173. In addition, in diagram 1129 box 1178 is shifted by an amount 1177 that is equal to time lag 1170. As such, in diagram 1129 the time lag 1170 is corrected. Now a product waveform can be derived by multiplying values of the time-shifted second ECG signal of diagram 1129, instead of multiplying values of the sensed second ECG signal 1126.

The time-shifting may be embedded in the programming of processor 230 or 330 or 1030, at the time that a patient is fitted. At that time the ECG signals can be free from noise. In particular, in some embodiments, processor 230 or 330 or 1030 can be further configured to detect a first test peak 1161 occurring in first ECG signal A, detect a second test peak 1171 occurring in second ECG signal B, and detect a time lag 1170 between first test peak 1161 and second test peak 1171. In such embodiments, second ECG signal B can be time-shifted according to time lag 1170 that was learned this way.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 12:
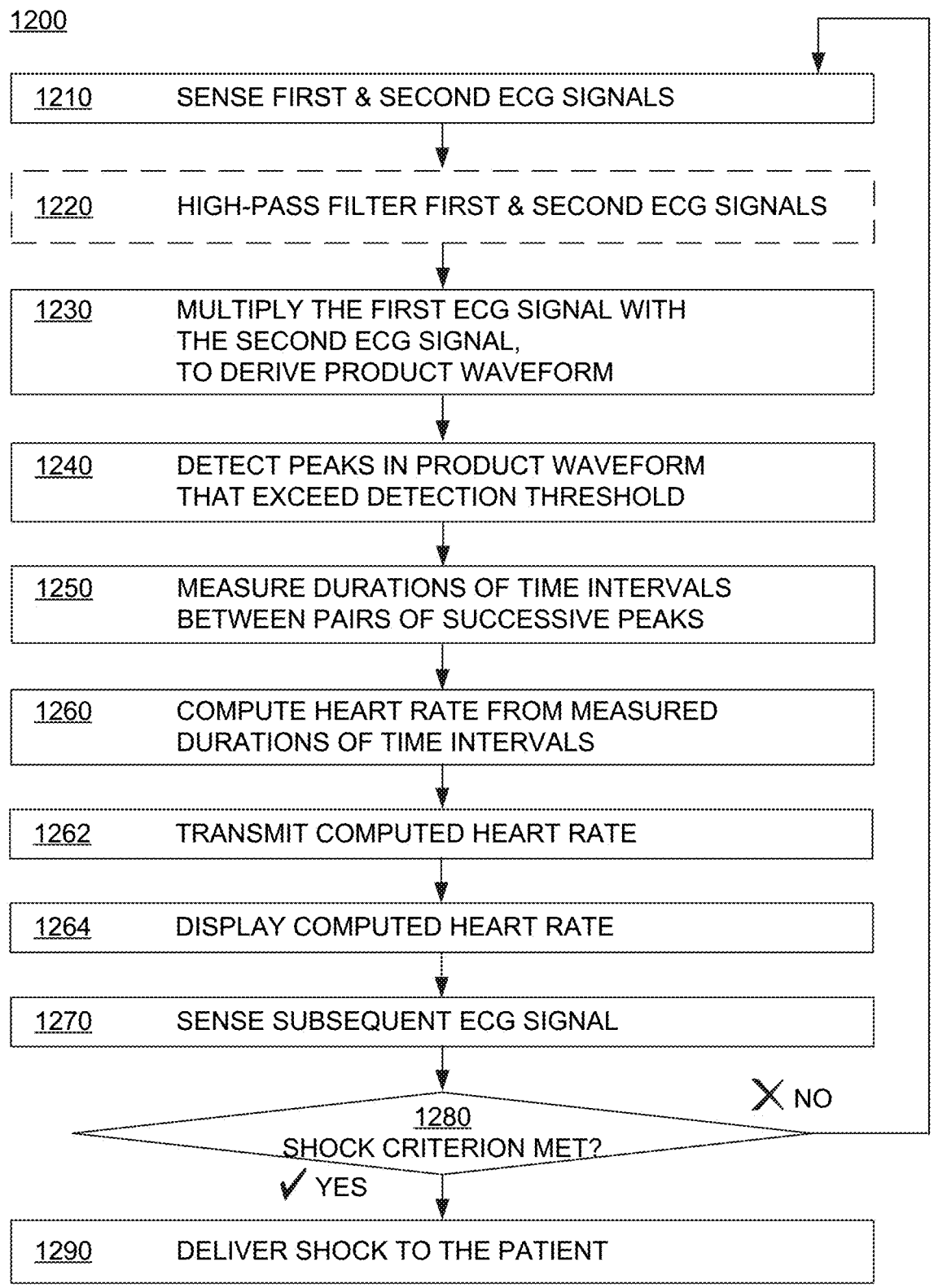
FIG. 12 is a flowchart for illustrating methods according to embodiments.

FIG. 12 shows a flowchart 1200 for describing methods according to embodiments. According to an operation 1210, a first ECG signal from a first vector and a second ECG signal from the second vector may be sensed or measured. The second ECG signal may be sensed substantially contemporaneously with sensing the first ECG signal. Sensing may be performed by electrodes, etc.

According to another, optional operation 1220, the first ECG signal and/or the second ECG signal may be high-pass filtered, to derive a high-pass filtered first ECG signal and/or a high-pass filtered second ECG signal.

According to another operation 1230, values of the first ECG signal may be multiplied with values of the second ECG signal to derive a product waveform. If optional operation 1220 has been performed, then the product waveform may be derived by multiplying values of the high-pass filtered first ECG signal instead of multiplying values of the first ECG signal, and so on with the second ECG signal.

According to another operation 1240, peaks may be detected in the product waveform, which exceed a detection threshold. The detection threshold may be as described above.

According to another operation 1250, durations may be measured, of time intervals between pairs of successive ones of the detected peaks. Sample such durations are durations 451-454 of FIG. 4.

According to another operation 1260, a heart rate of the patient may be computed. Computing may be from the measured durations of the time intervals, as described above. The computed heart rate may be stored in memory 238. Optionally the computed heart rate may be transmitted wirelessly by communication module 290. Optionally the computed heart rate may be displayed by a screen that implements user interface 280.

According to another, optional operation 1262, the heart rate computed at operation 1260 may be transmitted. Transmitting may be performed, for example, wirelessly by communication module 290.

According to another, optional operation 1264, the heart rate computed at operation 1260 may be displayed. Displaying may be performed, for example, by a screen of user interface 280.

According to another operation 1270, a subsequent ECG signal may be sensed after sensing the first ECG signal. The subsequent ECG signal may be sensed from any vector. Sensing may be performed by electrodes, etc. Of course, the ECG signal from either the first vector or the second vector may be considered to have a) an early portion that is considered to be the first or second ECG signal for operation 1230, and b) a subsequent portion that is considered to be the subsequent ECG signal. The subsequent signal may have less noise, for example be more similar to signal 501 than to the signal of diagram 419.

According to another operation 1280, it may be determined whether or not a shock criterion is met. The determination may be from the subsequent ECG signal or from the computed heart rate. The determination may be performed responsive to the value of the heart rate computed at operation 1260. If at operation 1280 the answer is "NO", indicated by a crossed-out mark, then execution may return to a previous operation, such as operation 1210.

If at operation 1280 the answer is "YES", indicated by a checkmark, then according to another operation 1290, responsive to the shock criterion being met the discharge circuit may be controlled to discharge the stored electrical charge through the patient. Discharging may be while the support structure is worn by the patient, so as to deliver a shock to the patient.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system, comprising:
    a support structure configured to be worn by an ambulatory patient;
    an energy storage module configured to store an electrical charge;
    a discharge circuit coupled to the energy storage module;
    electrodes configured to be attached at different locations of the patient's body so as to define at least a first vector and a second vector distinct from the first vector;
    a measurement circuit configured to sense a first Electrocardiogram (ECG) signal from the first vector, a second ECG signal from the second vector substantially contemporaneously with sensing the first ECG signal, and a subsequent ECG signal after sensing the first ECG signal; and
    a processor configured to:
        multiply values of the first ECG signal with values of the second ECG signal to derive a product waveform,
        detect, in the product waveform, peaks that exceed a detection threshold,
        measure durations of time intervals between pairs of successive ones of the detected peaks,
        compute a heart rate of the patient from the measured durations of the time intervals,
        determine from the subsequent ECG signal whether or not a shock criterion is met, and
    control, responsive to the shock criterion being met, the discharge circuit to discharge the stored electrical charge through the patient while the support structure is worn by the patient so as to deliver a shock to the patient; and
    a communication module configured to transmit wirelessly the computed heart rate.

2. The WCD system of claim 1, further comprising:
    a screen configured to display the computed heart rate.

3. The WCD system of claim 1, in which
the first ECG signal is high-pass filtered to derive a high-pass filtered first ECG signal, and
the product waveform is derived by multiplying values of the high-pass filtered first ECG signal instead of multiplying values of the first ECG signal.

4. The WCD system of claim 1, in which
the electrodes further define a third vector,
the measurement circuit is further configured to sense a third ECG signal from the third vector, and
the processor is further configured to:
multiply values of the third ECG signal with the values of the first ECG signal and of the second ECG signal to derive the product waveform.

5. The WCD system of claim 4, in which
the electrodes further define a fourth vector,
the measurement circuit is further configured to sense a fourth ECG signal from the fourth vector, and
the processor is further configured to:
multiply values of the fourth ECG signal with the values of the first ECG signal, of the second ECG signal and of the third ECG signal, to derive the product waveform.

6. The WCD system of claim 1, in which
when a peak is detected at a certain moment, no other peaks are detected for an inactive time period after the certain moment.

7. The WCD system of claim 1, in which
the detection threshold changes with time.

8. The WCD system of claim 1, in which
responsive to a certain one of the peaks being thus detected, a certain amplitude of the certain detected peak is input, and
the detection threshold is then established responsive to the input certain amplitude.

9. The WCD system of claim 1, in which
the second ECG signal is time-shifted with respect to the first ECG signal to derive a time-shifted second ECG signal, and
the product waveform is derived by multiplying values of the time-shifted second ECG signal instead of multiplying values of the sensed second ECG signal.

10. The WCD system of claim 9, in which
the processor is further configured to:
detect a first test peak occurring in the first ECG signal,
detect a second test peak occurring in the second ECG signal,
detect a time lag between the first test peak and the second test peak, and
in which the second ECG signal is time-shifted according to the time lag.

11. A wearable cardioverter defibrillator (WCD) system, comprising:
a support structure configured to be worn by an ambulatory patient;
an energy storage module configured to store an electrical charge;
a discharge circuit coupled to the energy storage module;
electrodes configured to be attached at different locations of the patient's body so as to define at least a first vector and a second vector distinct from the first vector;
a measurement circuit configured to sense a first Electrocardiogram (ECG) signal from the first vector, a second ECG signal from the second vector substantially contemporaneously with sensing the first ECG signal, and a subsequent ECG signal after sensing the first ECG signal;
a processor configured to:
multiply values of the first ECG signal with values of the second ECG signal to derive a product waveform,
detect, in the product waveform, peaks that exceed a detection threshold,
measure durations of time intervals between pairs of successive ones of the detected peaks,
compute a heart rate of the patient from the measured durations of the time intervals,
determine from the subsequent ECG signal whether or not a shock criterion is met, and
control, responsive to the shock criterion being met, the discharge circuit to discharge the stored electrical charge through the patient while the support structure is worn by the patient so as to deliver a shock to the patient; and
a screen configured to display the computed heart rate.

12. The WCD system of claim 11, in which
the first ECG signal is high-pass filtered to derive a high-pass filtered first ECG signal, and
the product waveform is derived by multiplying values of the high-pass filtered first ECG signal instead of multiplying values of the first ECG signal.

13. The WCD system of claim 11, in which
the electrodes further define a third vector,
the measurement circuit is further configured to sense a third ECG signal from the third vector, and
the processor is further configured to:
multiply values of the third ECG signal with the values of the first ECG signal and of the second ECG signal to derive the product waveform.

14. The WCD system of claim 13, in which
the electrodes further define a fourth vector,
the measurement circuit is further configured to sense a fourth ECG signal from the fourth vector, and
the processor is further configured to:
multiply values of the fourth ECG signal with the values of the first ECG signal, of the second ECG signal and of the third ECG signal, to derive the product waveform.

15. The WCD system of claim 11, in which
when a peak is detected at a certain moment, no other peaks are detected for an inactive time period after the certain moment.

16. The WCD system of claim 11, in which
the detection threshold changes with time.

17. The WCD system of claim 11, in which
responsive to a certain one of the peaks being thus detected, a certain amplitude of the certain detected peak is input, and
the detection threshold is then established responsive to the input certain amplitude.

18. The WCD system of claim 11, in which
the second ECG signal is time-shifted with respect to the first ECG signal to derive a time-shifted second ECG signal, and
the product waveform is derived by multiplying values of the time-shifted second ECG signal instead of multiplying values of the sensed second ECG signal.

19. The WCD system of claim 18, in which
the processor is further configured to:
detect a first test peak occurring in the first ECG signal,
detect a second test peak occurring in the second ECG signal,
detect a time lag between the first test peak and the second test peak, and in which the second ECG signal is time-shifted according to the time lag.

20. A non-transitory computer-readable storage medium storing one or more programs which, when executed by at least one processor of a wearable cardioverter defibrillator ("WCD") system, the WCD system further including a support structure configured to be worn by an ambulatory patient, an energy storage module that can store an electrical charge, a discharge circuit coupled to the energy storage module, electrodes attached at different locations of the patient's body so as to define at least a first vector and a second vector distinct from the first vector, and a measurement circuit, these one or more programs result in operations comprising:

sensing, by the electrodes, a first Electrocardiogram (ECG) signal from the first vector;

sensing a second ECG signal from the second vector substantially contemporaneously with sensing the first ECG signal;

multiplying values of the first ECG signal with values of the second ECG signal to derive a product waveform;

detecting, in the product waveform, peaks that exceed a detection threshold;

measuring durations of time intervals between pairs of successive ones of the detected peaks;

computing a heart rate of the patient from the measured durations of the time intervals;

sensing a subsequent ECG signal after sensing the first ECG signal;

determining from the subsequent ECG signal whether or not a shock criterion is met; and controlling, responsive to the shock criterion being met, the discharge circuit to discharge the stored electrical charge through the patient while the support structure is worn by the patient so as to deliver a shock to the patient.

21. A method for a wearable cardioverter defibrillator (WCD) system, the WCD system including a support structure configured to be worn by an ambulatory patient, an energy storage module storing an electrical charge, a discharge circuit coupled to the energy storage module, electrodes attached at different locations of the patient's body so as to define at least a first vector and a second vector distinct from the first vector, a measurement circuit and a processor, the method comprising:

sensing, by the electrodes, a first Electrocardiogram (ECG) signal from the first vector;

sensing a second ECG signal from the second vector substantially contemporaneously with sensing the first ECG signal;

multiplying values of the first ECG signal with values of the second ECG signal to derive a product waveform;

detecting, in the product waveform, peaks that exceed a detection threshold;

measuring durations of time intervals between pairs of successive ones of the detected peaks;

computing a heart rate of the patient from the measured durations of the time intervals;

sensing a subsequent ECG signal after sensing the first ECG signal;

determining from the subsequent ECG signal whether or not a shock criterion is met; and controlling, responsive to the shock criterion being met, the discharge circuit to discharge the stored electrical charge through the patient while the support structure is worn by the patient so as to deliver a shock to the patient.

* * * * *